(12) United States Patent
Takahashi et al.

(10) Patent No.: US 8,629,122 B2
(45) Date of Patent: Jan. 14, 2014

(54) NUCLEUS PULPOSUS FILLER

(75) Inventors: Katsuya Takahashi, Higashiyamato (JP); Tomoya Sato, Higashiyamato (JP); Yukihiro Matsuyama, Nagoya (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 13/092,716

(22) Filed: Apr. 22, 2011

(65) Prior Publication Data

US 2011/0201570 A1  Aug. 18, 2011

Related U.S. Application Data

(63) Continuation of application No. 11/579,673, filed as application No. PCT/JP2005/008179 on Apr. 28, 2005.

(30) Foreign Application Priority Data

May 7, 2004 (JP) .................................. 2004-138034

(51) Int. Cl.
*A01N 43/04* (2006.01)

(52) U.S. Cl.
USPC .......................................................... 514/55

(58) Field of Classification Search
None
See application file for complete search history.

(56) References Cited

U.S. PATENT DOCUMENTS

| | | | |
|---|---|---|---|
| 5,137,733 A | 8/1992 | Noda et al. | |
| 5,462,976 A | 10/1995 | Matsuda et al. | |
| 6,458,889 B1 * | 10/2002 | Trollsas et al. | 525/54.1 |
| 6,719,797 B1 | 4/2004 | Ferree | |
| 2003/0095994 A1 * | 5/2003 | Geistlich et al. | 424/426 |
| 2003/0181365 A1 * | 9/2003 | Slivka et al. | 514/12 |
| 2004/0076811 A1 | 4/2004 | Sato | |
| 2006/0252925 A1 | 11/2006 | Sato | |

FOREIGN PATENT DOCUMENTS

| | | |
|---|---|---|
| EP | 1 369 441 A1 | 12/2003 |
| JP | 6-73102 A | 3/1994 |
| JP | 2000-502380 A | 2/2000 |
| JP | 2003-299741 A | 10/2003 |
| JP | 2003-530364 A | 10/2003 |
| WO | 02/060971 A | 1/2002 |
| WO | 02/40070 A2 | 5/2002 |
| WO | 2004/029137 A2 | 4/2004 |

OTHER PUBLICATIONS

"gel". Oxford Dictionaries. Apr. 2010. Oxford Dictionaries. Apr. 2010. Oxford University Press. May 21, 2012) http://oxford-dictionaries.com/definition/gel>.*
Japanese Office Action issued on Jan. 11, 2011 from the Japan Patent Office in a counterpart Japanese application No. 2006-512979.
Supplementary European Search Report dated Jun. 30, 2011, issued from European Patent Office in a counterpart application No. 05737288.0.

* cited by examiner

*Primary Examiner* — Layla Bland
(74) *Attorney, Agent, or Firm* — Sughrue Mion, PLLC

(57) ABSTRACT

The present invention provides a nucleus pulposus filler or the like which is to be packed into an area in deformed intervertebral disc wherein normal nucleus should be located and can be stabley maintained for a long time More preferably, the present invention provides a nucleus pulposus filler comprising a crosslinked chondroitin sulfate as an active ingredient. The photocrosslinked chondroitin sulfate is preferably the following one: a photocrosslinked chondroitin sulfate obtainable by freezing a photoreactive chondroitin sulfate-containing solution comprising: a photoreactive chondroitin sulfate to which a photoreactive group is bound; an aqueous solvent capable of dissolving the photoreactive chondroitin sulfate; and any one substance selected from the group consisting of an alcohol having aqueous solvent miscibility, a surfactant, and a cheleting agent; irradiating the resulting frozen product with light; and then melting the frozen product. The filler can be provided as a kit by packing it into a container from which the filler can be pushed out.

10 Claims, No Drawings

NUCLEUS PULPOSUS FILLER

CROSS REFERENCE TO RELATED APPLICATION

This is a continuation application of U.S. application Ser. No. 11/579,673 filed Jun. 10, 2008, which is a 371 Application of PCT/JP2005/008179 filed Apr. 28, 2005, which claims priority of Japanese Application No. 2004-138034 filed May 7, 2004. The above-noted applications are incorporated herein by reference in their entirety.

TECHNICAL FIELD

The present invention relates to a nucleus pulposus filler comprising a crosslinked chondroitin sulfate as an active ingredient.

BACKGROUND ART

First, abbreviations used herein will be described.
CS: Chondroitin sulfate
CS-A: Chondroitin sulfate A (chondroitin 4-sulfate; chondroitin sulfate containing, as a main constitutional disaccharide unit, a disaccharide structure comprising a glucuronic acid residue and an N-acetylgalactosamine residue sulfated at the C-4 position)
CS-B: Chondroitin sulfate B (dermatan sulfate; chondroitin sulfate containing, as a main constitutional disaccharide unit, a disaccharide structure comprising an iduronic acid residue and an N-acetylgalactosamine residue sulfated at the C-4 position)
CS-C: Chondroitin sulfate C (chondroitin 6-sulfate; chondroitin sulfate containing, as a main constitutional disaccharide unit, a disaccharide structure comprising a glucuronic acid residue and an N-acetylgalactosamine residue sulfated at the C-6 position)
CS-D: Chondroitin sulfate D (chondroitin sulfate containing, as a main constitutional disaccharide unit, a disaccharide structure comprising a glucuronic acid residue sulfated at the C-2 position and an N-acetylgalactosamine residue sulfated at the C-6 position)
CS-E: Chondroitin sulfate E (chondroitin sulfate containing, as a main constitutional disaccharide unit, a disaccharide structure comprising a glucuronic acid residue and an N-acetylgalactosamine residue sulfated at the C-4 and C-6 positions)
CS-K: Chondroitin sulfate K (chondroitin sulfate containing, as a main constitutional disaccharide unit, a disaccharide structure comprising a glucuronic acid residue sulfated at the C-3 position and an N-acetylgalactosamine residue sulfated at the C-4 position)
EDCI.HCl: 1-Ethyl-3-(3-dimethylaminopropyl)carbodiimide hydrochloride
HA: Hyaluronic acid
Crosslinked CS: CS which is crosslinked
Photo crosslinked CS: CS which is crosslinked by irradiation with light
Photocrosslinking reaction: Reaction wherein crosslinking is formed by irradiation with light
Photoreactive group: Residue of a part at which crosslinking is formed in a compound wherein the crosslinking is formed by irradiation with light
Photoreactive CS: CS into which a photoreactive group is introduced and which possesses a property capable of forming crosslinking by irradiation with light
HOSu: N-Hydroxysuccinimide
PBS: Phosphate-buffered physiological saline
PEG: Polyethylene glycol Moreover, the "nucleus pulposus filler" means a pharmaceutical agent to be packed into an area where nucleus pulposus of an intervertebral disc is present. In this connection, the term "fill" in the present specification and claims is used as a concept including not only the case that a predetermined area is completely charged but also the case that the area is not completely charged.

Deformation of an intervertebral disc is one of major causes of spinal diseases, wherein an area where nucleus pulposus is present and which shows a gel-like property in a normal state loses its gel-like property and thereby symptoms such as pain (e.g., backache) may be induced. Against such pain derived from the deformation of an intervertebral disc, one should perform rehabilitation exercise for controlling the pain or wait the time when the spine is fixed.

If the area where normal nucleus pulposus is to be present can regain a gel-like composition and the composition can be maintained for a long period of time in the deformed intervertebral disc, improvement of pain (backache or the like) over a long period of time can be expected from the biomechanical viewpoint and from the viewpoint of functional maintenance of the intervertebral disc.

Moreover, even in the spinal surgical field, there has been studied tissue regeneration using intervertebral disc cells. If the area where normal nucleus pulposus is to be present can regain a gel-like composition and the composition can be maintained for a long period of time in the deformed intervertebral disc, a good environment for regeneration of nucleus pulposus can be formed over a long period of time and it can be also expected that a good nucleus pulposus is efficiently regenerated.

Furthermore, if the area where nucleus pulposus of an intervertebral disc is to be present can maintain a gel-like composition for a long period of time, there is also a possibility that the deformation of the intervertebral disc can be prevented and spinal diseases themselves can be controlled.

Patent Document 1 discloses restoration of injury and deformation of an intervertebral disc by injecting CS or HA into nucleus pulposus.

However, there is neither disclosure nor suggestion on injection of a crosslinked CS into nucleus pulposus of an intervertebral disc.

Patent Document 1: WO 02/40070 pamphlet

DISCLOSURE OF THE INVENTION

Problems to be Solved by the Invention

An object of the present invention is to provide a nucleus pulposus filler which is maintained for a long period of time in an area where nucleus pulposus of an intervertebral disc is present.

Means for Solving the Problems

As a result of the extensive studies for solving the above problems, the present inventors have found that a crosslinked CS is remarkably maintained for a long period of time in an area where nucleus pulposus of an intervertebral disc is present and thus have provided the present invention.

Namely, the present invention provides a nucleus pulposus filler comprising a crosslinked CS as an active ingredient (hereinafter referred to as "filler of the present invention"). The crosslinking is preferably photocrosslinking.

Moreover, the photocrosslinked CS is preferably the following one:

a photocrosslinked CS obtainable by freezing a photoreactive CS-containing solution comprising:

a photoreactive CS to which a photoreactive group is bound;

an aqueous solvent capable of dissolving the photoreactive CS; and any one substance selected from the group consisting of an alcohol having aqueous solvent miscibility, a surfactant, and a cheleting agent, irradiating the resulting frozen product with light; and then melting the frozen product.

The alcohol used herein is preferably an alcohol having a property of keeping a frozen state at a temperature of −7° C. or lower in the case that the alcohol is added to the above aqueous solvent solution of the photoreactive CS, the whole is frozen to obtain a frozen body, and then the temperature is elevated. Moreover, the alcohol is preferably one represented by the following formula (I):

R—OH  (1)

wherein R is selected from the group consisting of:
a linear alkyl having 1 to 10 carbon atoms,
a branched alkyl having 3 to 10 carbon atoms,
—CH$_2$—(CHOH)$_1$—CH$_2$OH, wherein 1 is an integer of 0 to 5,

wherein m is integer of 3 to 5, and
—(CH$_2$CH$_2$O)$_n$—H, wherein n is an integer of 3 to 70.

The surfactant used herein is preferably a nonionic surfactant or an anionic surfactant. In the case of using a nonionic surfactant, the surfactant is preferably polyethylene glycol. In the case of using an anionic surfactant, the surfactant is preferably an alkyl sulfate salt.

The cheleting agent used herein is preferably an hydroxycarboxylic acid or a polyaminocarboxylic acid. In the case of using an hydroxycarboxylic acid, the agent is preferably citric acid or a salt thereof. In the case of using a polyaminocarboxylic acid, the agent is preferably ethylenediamine tetraacetio acid.

The weight average molecular weight of CS in the crosslinked CS is preferably from 10,000 to 100,000.

The photoreactive group in the photoreactive CS is preferably bound to the carboxyl group of CS.

The photoreactive CS is preferably contained in an amount of 1 to 20% by weight in the photoreactive CS-containing solution.

As the crosslinked CS, one further having the following properties is preferred:

Viscosity measured under conditions of 20° C. and standard corn (1 degree) by means of a rotary viscosimeter is from 300 to 30,000 mPa·S and the CS shows a gel form.

The filler of the present invention is preferably administrated by injection.

Furthermore, the filler of the present invention is preferably used for regeneration of nucleus pulposus.

Moreover, the present invention provides a nucleus pulposus filler kit comprising the filler of the present invention and a container from which the filler can be pushed out, wherein the filler is packed into the container (hereinafter referred to as "kit of the present invention").

Effect of the Invention

When the filler of the present invention is used, an area where normal nucleus pulposus is to be present can be made a gel-like composition in a deformed intervertebral disc and the composition can be maintained for a long period of time. Therefore, the filler can be utilized for improvement of pain (backache) over a long period of time through improvement in a biomechanical aspect and improvement in function of an intervertebral disc, and thus is extremely useful.

Also, the filler of the present invention makes an area where normal nucleus pulposus is to be present a gel-like composition in a deformed intervertebral disc and the composition can be maintained for a long period of time. Therefore, a good environment for nucleus pulposus regeneration is formed over a long period of time and thus the filler can be utilized for regenerative medicine of nucleus pulposus and the like, so that it is extremely useful.

Furthermore, since the filler of the present invention can maintain the area where nucleus pulposus of intervertebral disc is present as a gel-like composition for a long period of time, the filler can be applied to prevention of deformation of an intervertebral disc, control of spinal diseases themselves, and the like, and thus it is extremely useful.

Moreover, when the kit of the present invention is used, the filler of the present invention can be conveniently and rapidly administrated, so that the kit is extremely useful.

BEST MODE FOR CARRYING OUT THE INVENTION

<1> Active Ingredient of Filler of the Present Invention

The filler of the present invention is a nucleus pulposus filler comprising a crosslinked CS as an active ingredient. With regard to the crosslinked CS used herein, the crosslinking mode, the crosslinking method, the form of the crosslinked CS (gel-like, sponge-like, etc.), and the like are not particularly limited as far as CS is crosslinked.

CS to be crosslinked is not particularly limited as far as it contains, as a main skeleton, a disaccharide repeating structure comprising an N-acetylgalactosamine residue and a glucuronic acid residue (or an iduronic acid residue) and is recognized to be CS in the technical field of the present invention. As such CS, examples thereof include CS-A, CS-B, CS-C, CS-D, CS-E, and CS-K. CS to be crosslinked may be a mixture containing these CS's.

The sources of such CS are not particularly limited and any of naturally occurring ones, chemically synthesized ones, ones produced by microorganisms such as yeasts according to gene engineering methods, and the like can be used. For example, in the case of obtaining CS from a natural substance, the natural substance to be a raw material can be suitably selected. For example, CS-A can be obtained from sturgeon notochord, whale cartilage, shark cartilage, or the like; CS-B from pig skin, chicken crest, or the like; CS-C and CS-D from shark cartilage or the like; CS-E from squid cartilage; CS-K from horseshoe crab cartilage or the like. Among these, CS derived from shark cartilage is preferably used.

The weight average molecular weight of the CS to be crosslinked is also not particularly limited but is preferably from 10,000 to 100,000, more preferably from 20,000 to 50,000.

The crosslinked CS can be produced by introducing a crosslinking group into such CS, followed by inducing a crosslinking reaction.

For example, as one example of crosslinking CS, there may be exemplified a method of effecting crosslinking using diglycidyl ether as a crosslinking agent (*Eur. J. Pharm Sci*, March; 15(2): 139-48 (2002)), a method of combining a photoreactive crosslinking agent with CS to obtain a photoreactive CS, purifying it to remove the unreacted crosslinking agent, and successively irradiating purified one with light to effect crosslinking (JP-A-6-73102), a method of combining a photoreactive crosslinking agent with CS to obtain a photoreactive CS, dissolving it in an aqueous solvent and freezing it, and successively irradiating it with light with maintaining the frozen state to effect crosslinking (a crosslinked glycosaminoglycan showing a sponge property is obtained by this method) (WO02/060971).

All these methods can be adopted but it is preferred to effect crosslinking by irradiation with light (photocrosslinking).

The crosslinking group to be introduced into CS beforehand in the case of photocrosslinking is not particularly limited as far as it is a photoreactive group but the crosslinking group is preferably a residue of a compound capable of inducing a photodimerization reaction or a photopolymerization reaction by irradiation with UV light. As such a compound, there may be exemplified cinnamic acid, substituted cinnamic acids, acrylic acid, acrylic acid derivatives, maleic acid, fumaric acid, sorbic acid, coumarin, thymine, and the like. In this connection, as the substituted succininc acids, there may be mentioned, for example, aminocinnamic acids, e.g., p-aminocinnamic acid, which are cinnamic acids wherein any of the hydrogen atoms on the benzene ring is substituted with an amino group. As the acrylic acid derivatives, there may be exemplified thiopheneacrylic acid, furylacrylic acid, and the like.

Among these photoreactive groups, preferred are those having a vinylene group capable of forming a cyclobutane ring by a photoreaction and more preferred is cinnamic acid or a substituted cinnamic acid from the viewpoint of photoreactivity and safety. As the substituted cinnamic acid, an aminocinnamic acid is preferred.

Moreover, at the formation of the photoreactive CS, a molecule which are bound to both the photoreactive group and CS for keeping a certain distance (a spacer) may be contained. The photoreactive CS to be used in the present invention is preferably one wherein the photoreactive group is bound to CS through the spacer. Therefore, as the photoreactive CS, most preferred is CS to which a cinnamic acid or substituted cinnamic acid bound to a spacer is bound through the spacer.

Specific examples of such a "cinnamic acid or substituted cinnamic acid bound to a spacer" include cinnamic acid aminoalkyl ester derivatives wherein an amino alcohol ($H_2N$—$(CH_2)_p$—OH: p=1 to 18, or $H_2N$—$(CH_2$—$O)_q$—$CH_2$—OH: q=1 to 9) is bound to the carboxyl group of cinnamic acid through an ester bond, derivatives wherein a diamine ($H_2N$—$(CH_2)_r$—$NH_2$: r=1 to 10) or a diol (HO—$(CH_2)_s$—OH: s=1 to 10) is introduced into cinnamic acid or a substituted cinnamic acid, derivatives wherein an amino acid (HOOC—$(CHR)_t$—$NH_2$: t=1 to 10, R represents a substituent in the α-position of a natural-type amino acid, such as an alkyl group or a hydroxyalkyl group), a peptide, or the like is introduced into a substituted cinnamic acid (e.g., aminocinnamic acid or the like), and the like. Among these, preferred are derivatives wherein an amino alcohol is introduced into the carboxyl group of cinnamic acid (cinnamic acid aminoalkyl esters). The amino alcohol is preferably an amino alcohol represented by the above general formula wherein n is 1 to 18, and particularly preferred is an amino alcohol represented by the above general formula wherein n is 3 to 6 and extremely preferred is an amino alcohol represented by the formula wherein n is 3 to 4.

In this case, the position in the CS molecule to which the photoreactive group is introduced can be suitably selected depending on the functional group possessed by the spacer bound to the photoreactive group and is not particularly limited, but the amino group (present as an acetylamino group or a sulfamino group), hydroxyl group, carboxyl group, or the like in the CS molecule may be exemplified. For example, in the case that a cinnamic acid aminoalkyl ester is used as the "photoreactive group bound to a spacer", the photoreactive group can be introduced into CS through a spacer by combining the amino group of the aminoalkyl with the carboxyl group in the CS molecule through an amide bond.

The introduction ratio of the photoreactive group to be introduced into CS is from 0.1 to 75%, preferably from 0.3 to 70%. The introduction reaction of the photoreactive group into CS can be carried out by the method described in JP-A-6-073102, for example. The value of the introduction ratio can be suitably changed or controlled by controlling the number of moles of CS to be reacted and the number of moles of the photoreactive group. In this connection, the introduction ratio of the photoreactive group can be calculated according to the method described in Example 1 to be mentioned below. Moreover, the crosslinking ratio of the photocrosslinked CS is from 1 to 75%, preferably from 15 to 50%. The crosslinking ratio can be calculated according to the method described in Example 1 to be mentioned below.

Among such photocrosslinked CS, the following is preferred:

a photocrosslinked CS obtainable by freezing a photoreactive CS-containing solution comprising:

a photoreactive CS to which a photoreactive group is bound;

an aqueous solvent capable of dissolving the photoreactive CS; and any one substance selected from the group consisting of an alcohol having aqueous solvent miscibility, a surfactant, and a cheleting agent;

irradiating the resulting frozen product with light; and then melting the frozen product.

The alcohol used herein is not particularly limited as far as it is miscible with an aqueous solvent but is preferably an alcohol having a property of keeping the frozen state at −7° C. or lower in the case that the alcohol is added to the above aqueous solvent solution of the photoreactive CS, the whole is frozen to obtain a frozen body, and then the temperature is elevated. In particular, the alcohol is preferably one represented by the following formula (I):

R—OH            (1)

Wherein R is selected from the group consisting of:

a linear alkyl having 1 to 10 carbon atoms, a branched alkyl having 3 to 10 carbon atoms, —$CH_2$—$(CHOH)_1$—$CH_2OH$, wherein 1 is an integer of 0 to 5,

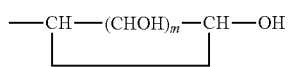

wherein m is an integer of 3 to 5, and
—(CH$_2$CH$_2$O)$_n$—H, wherein n is an integer of 3 to 70.

The "surfactant" used herein is not particularly limited as far as it is miscible with an aqueous solvent but is preferably a nonionic surfactant or an anionic surfactant. In the case of using a nonionic surfactant, the surfactant is preferably polyethylene glycol. In the case of using an anionic surfactant, the surfactant is preferably an alkyl sulfate salt.

The cheleting agent used herein is not particularly limited as far as it is miscible with an aqueous solvent but is preferably an hydroxycarboxylic acid or a polyaminocarboxylic acid. In the case of using an hydroxycarboxylic acid, the agent is preferably citric acid or a salt thereof. In the case of using a polyaminocarboxylic acid, the agent is preferably ethylenediamine tetraacetic acid.

The photoreactive CS is preferably contained in an amount of 1 to 20% by weight in the photoreactive CS-containing solution.

As the crosslinked CS which may be a raw material for the filler of the present invention, one further having the following properties is preferred:

Viscosity measured under conditions of 20° C. and standard corn (1 degree) by means of a rotary viscosimeter is from 300 to 30,000 mPa·S and the CS shows a gel form.

<2> Form of Filler of the Present Invention and the Like

The mixing amount of the crosslinked CS in the filler of the present invention is also not particularly limited. Therefore, the crosslinked CS can be used as the filler of the present invention as it is or the crosslinked CS can be used as the filler of the present invention after a medically or pharmaceutically acceptable solvent is added thereto as far as it does not affect adversely on the crosslinked CS and does not have any effect on the advantages of the present invention.

In addition, there can be used other ingredients which are used in medicaments, such as other pharmaceutically active ingredients and conventional stabilizers, emulsifiers, osmotic pressure-regulators, buffering agents, isotonic agents, preservatives, anesthetics, colorants, excipients, binders, lubricants, disintegrators, and fragrant materials, as far as they do not affect adversely on the crosslinked CS and do not have any effect on the advantages of the present invention. The formulation of the filler of the present invention can be performed by using a known method.

<3> Subject of the Filler of the Present Invention to be Administrated, Etc.

Since the filler of the present invention is packed into a nucleus pulposus area of an intervertebral disc, the filler is administrated to vertebrates. Of vertebrates, it is preferably administrated to mammals, and particularly preferably administrated to human.

The filler of the present invention is administrated for the purpose of filling an area where normal nucleus pulposus is to be present in a deformed intervertebral disc in these animals. Therefore, the administration method is not particularly limited as far as the area is filled with the filler of the present invention but the filler is preferably administrated by injection.

The dosage per one administration, administration intervals, and the like of the filler of the present invention are individually determined depending on the administration method, administration form, administration purpose, and the like of the filler of the present invention, the age, sex, body weight, specific clinical conditions, and the like of subject animals to be administrated, and the like and thus is not particularly limited. For example, the filler can be usually administrated in an amount of from about 1 ml to 4 ml per adult, 1 to several times.

The filler of the present invention is maintained for a long period of time instead of deformed nucleus pulposus by filling the filler of the present invention and thus improvement of pain (backache etc) over a long period of time can be expected from the biomechanical viewpoint and from the viewpoint of functional maintenance of an intervertebral disc.

Moreover, an area wherein normal nucleus pulposus is to be present can be made a gel-like composition in a deformed intervertebral disc and the composition can be maintained for a long period of time. Therefore, an environment suitable for nucleus pulposus regeneration is formed for a long period of time and thus regeneration of good nucleus pulposus can be efficiently expected. The filler of the present invention is preferably used for regeneration of nucleus pulposus.

Furthermore, there is also a possibility that deformation of an intervertebral disc can be prevented and spinal diseases themselves can be controlled.

<4> Kit of the Present Invention

The kit of the present invention is a nucleus pulposus filler kit comprising the filler of the present invention and a container from which the filler can be pushed out, wherein the filler is packed into the container.

The "container from which the filler can be pushed out" is not particularly limited as far as it is a container from which the filler of the present invention packed into the container can be pushed out. For example, a syringe for injection and the like can be exemplified.

The method for filling the filler of the present invention into the above-mentioned container is also not particularly limited and can be suitably selected depending on the kind of the container.

The filler of the present invention can be conveniently and rapidly administrated by using the kit of the present invention.

Example 1

The following will specifically describe Example of the present invention. However, the technical scope of the present invention is not limited thereby.

<1> Materials, Methods and the Like

First, substances to be tested, analytical methods, and the like used in the present Example will be described.

(1) Substances to be Tested (1-1) Crosslinked CS

As a crosslinked CS, there was used one produced as follows.

(1) Five grams of CS derived from shark cartilage (manufactured by Seikagaku Corporation, weight average molecular weight of about 30,000) was dissolved in 150 mL of distilled water. After 75 mL of 1,4-dioxane was added, 13.7 g of HOSu, 11.4 mg of EDCl.HCl, 14.4 g of aminopropyl cinnamate hydrochloride were successively added thereto, followed by a reaction at room temperature for 3 hours. After 4 g of NaCl was added, ethanol was poured thereinto to deposit a precipitate. After the precipitate was washed and recovered, it was dried at 40° C. under reduced pressure to obtain 4 g of a photoreactive CS. The introduction ratio of the photoreactive group calculated according to the method to be mentioned below was 32.4%.

(2) After the photoreactive CS obtained above was dissolved in water for injection so that the weight concentration became 4%, PEG 400 was added so that the weight concentration became 2%, and then dissolved to form a solution for reaction. After the solution for reaction was filtrated through a 0.22 μm membrane filter (manufactured by Nihon Millipore K.K.), the solution was poured into glass plates whose gap was adjusted to be 1 mm and then frozen under an atmosphere of −20° C. With maintaining the frozen state, UV irradiation was conducted by means of an 800 W high-pressure mercury lamp (manufactured by ORC Manufacturing Co., Ltd.) so that irradiated light intensity became 5000 mJ/cm$^2$. After the irradiation, the temperature was returned to room temperature to effect melting, whereby a gel-form photocrosslinked CS composition was obtained. The crosslinking ratio calculated according to the method to be mentioned below was 33%. Furthermore, when viscosity under conditions of corn (1 degree) and 20° C. was measured by means of a rotary viscosimeter, the rotary viscosity of the sample (1 mL) was 3840.0 mPa.

(1-2) 1% Sodium HA (Trade Name: Artz, Manufactured by Seikagaku Corporation)

(2) Method for Calculating Introduction Ratio of Photoreactive Group

The introduction ratio of a photoreactive group in CS means a value represented as percentage of the number of the photoreactive groups introduced per a repeating disaccharide unit of CS. The amount of CS required for calculation of the introduction ratio was measured by a carbazole-measuring method utilizing a calibration curve and the amount of cinnamic acid in the case that cinnamic acid was used as a photoreactive group was measured by an absorbance-measuring method (measuring of 269 nm) utilizing a calibration curve. In the case that it was impossible to utilize the carbazole-measuring method, the amount was measured by a drying weight-loss method utilizing a calibration curve.

(3) Method for Calculating Crosslinking Ratio

With regard to the crosslinking ratio, after 1 g of a substance to be tested was saponified with 1 mL of 1 mol/L sodium hydroxide for 1 hour, the resulting solution was acidified, substances derived from the photoreactive group (monomer and dimer of the photoreactive group) were extracted with ethyl acetate, the substances were analyzed by high-performance liquid chromatography (HPLC), and the amount of the dimer was measured utilizing a calibration curve. Then, the number of moles of the photoreactive group which was converted into dimer relative to the photoreactive group introduced into CS was calculated as percentage (%).

(4) Preparation of Animal Model

Using 8-week-old Japan white house rabbits (body weight of about 2 to 2.5 kg), nucleus pulposus of an intervertebral disc was burst by pricking four intervertebral places (between L3 and L4, between L4 and L5, between L5 and L6, and between L6 and L7) in third to seventh intervertebral discs (L3 to L7) of third to seventh lumbar vertebras with a needle having a thickness of 18 gauge under X-ray radiographic guidance, whereby rabbit intervertebral disc deformation models were prepared. After about 2 weeks, it was confirmed under X-ray radiographic guidance that the intervertebral discs were narrowed.

(5) Pharmacological Test

About 300 µL of each substance to be tested was injected into the parts of burst nucleus pulposus in the model prepared in the above (4) under X-ray radiographic guidance. In the following, the group where the crosslinked CS gel was injected is referred to as a crosslinked CS gel group, the group where 1% sodium HA was injected is referred to as an HA-injected group, and the group where PBS was injected is referred to as a PBS group. In each group, 5 animals were used.

The lumbar vertebra part was photographed by MRI before injection of the substance to be tested, immediately after the injection, and one month and three months after the injection, and each nucleus pulposus part was observed. A high luminance on the MRI image shows that water is maintained and a low luminance shows that water is lost.

As a result, one month after the injection, the luminance on the MRI image at the nucleus pulposus part was kept high even when any of the crosslinked CS gel, 1% sodium HA, and PBS was used as the substance to be tested. Therefore, it was confirmed that water was maintained at the nucleus pulposus part one month after the injection and these substances to be tested were left and maintained. However, three months after the injection, a high luminance was maintained only in the case of the crosslinked CS gel. Accordingly, three months after the injection, it was confirmed that water was maintained only in the group of the crosslinked CS gel and thus the crosslinked CS gel alone was left and maintained.

Moreover, after the photographic recording by MRI, slice specimens of nucleus pulposus and surrounding parts thereof were prepared, which were stained with safranine-O and pathohistologically investigated. As a result, similarly to the results on MRI, in the group wherein the crosslinked CS gel was administrated, it was observed that inner parts of annulus fibrous of intervertebral discs showed a high stainability and thus the substance to be tested was left and maintained. Furthermore, based on the results, it was suggested that the injection of a crosslinked CS gel into a deformed intervertebral disc might suppress deformation of the inner tissues of annulus fibrous.

While the invention has been described in detail and with reference to specific embodiments thereof, it will be apparent to one skilled in the art that various changes and modifications can be made therein without departing from the spirit and scope thereof.

This application is based on Japanese patent application No. 2004-138034 filed on May 7, 2004 the entire contents of which are incorporated hereinto by reference.

INDUSTRIAL APPLICABILITY

The filler of the present invention can be utilized as an "alternative material for nucleus pulposus" capable of being stably maintained for a long period of time. Thereby, there is also a possibility of utilization for improvement of pain (backache) over a long period of time through improvement in a biomechanical aspect and improvement in function of an intervertebral disc. Furthermore, there are also possibilities of utilization for regeneration medicine of nucleus pulposus and the like and utilization for prevention of deformation of an intervertebral disc and control of spinal diseases themselves. In addition, the kit of the present invention can be utilized in the case that the filler of the present invention is intended to be conveniently and rapidly administrated.

The invention claimed is:

1. A method of regenerating nucleus pulposus in an area where normal nucleus pulposus is to be present in a deformed intervertebral disc in an animal, the method comprising administering a nucleus pulposus filler comprising a photocrosslinked chondroitin sulfate as an active ingredient for regeneration, whereby the nucleus pulposus is regenerated;
  wherein the photocrosslinked chondroitin sulfate is obtained by:
    freezing a chondroitin sulfate to which a cinnamic acid or substituted cinnamic acid bound to a spacer is bound to through the spacer-containing solution comprising:
    the chondroitin sulfate to which the cinnamic acid or substituted cinnamic acid bound to a spacer is bound to through the spacer;

an aqueous solvent capable of dissolving the chondroitin sulfate to which the cinnamic acid or substituted cinnamic acid bound to a spacer is bound to through the spacer; and any one substance selected from the group consisting of an alcohol having aqueous solvent miscibility, a surfactant, and a chelating agent;

irradiating the resulting frozen product with light; and then melting the frozen product, and wherein the photocrosslinked chondroitin sulfate has the following properties:

viscosity measured under conditions of 20° C. and standard corn (1 degree) by means of a rotary viscosimeter is from 300 to 30,000 mPa·S and the chondroitin sulfate has a gel form;

and the nucleus pulposus filler is administered by injection.

2. The method according to claim 1, wherein the alcohol is an alcohol having a property of keeping a frozen state at a temperature of −7° C. or lower in the case that the alcohol is added to the aqueous solvent solution of the chondroitin sulfate, the whole is frozen to obtain a frozen body, and then the temperature is elevated.

3. The method according to claim 1, wherein the alcohol is one represented by the following formula (I):

R—OH     (1)

wherein R is selected from the group consisting of:
a linear alkyl having 1 to 10 carbon atoms,
a branched alkyl having 3 to 10 carbon atoms,
—CH$_2$—(CHOH)$_1$—CH$_2$OH, wherein l is an integer of 0 to 5,

wherein m is an integer of 3 to 5, and
—(CH$_2$CH$_2$O)$_n$—H, wherein n is an integer of 3 to 70.

4. The method according to claim 1, wherein the surfactant is a nonionic surfactant or an anionic surfactant.

5. The method according to claim 4, wherein the nonionic surfactant is polyethylene glycol, and the anionic surfactant is an alkyl sulfate salt.

6. The method according to claim 1, wherein the chelating agent is an hydroxycarboxylic acid or a polyaminocarboxylic acid.

7. The method according to claim 6, wherein the hydroxycarboxylic acid is citric acid or a salt thereof, and the polyaminocarboxylic acid is ethylenediamine tetraacetic acid.

8. The method according to claim 1, wherein the chondroitin sulfate has a weight average molecular weight of 10,000 to 100,000.

9. The method according to claim 1, wherein the cinnamic acid or substituted cinnamic acid group in the chondroitin sulfate is bound to a carboxyl group of the chondroitin sulfate.

10. The method according claim 1, wherein the chondroitin sulfate is contained in an amount of 1 to 20% by weight in the chondroitin sulfate to which a cinnamic acid or substituted cinnamic acid bound to a spacer is bound to through the spacer-containing solution.

* * * * *